United States Patent [19]
Guthrie

[11] Patent Number: 5,789,910
[45] Date of Patent: Aug. 4, 1998

[54] MOLTEN METAL INCLUSION SENSOR PROBES

[75] Inventor: Roderick I. L. Guthrie, Westmount, Canada

[73] Assignee: R. Guthrie Research Associates Inc., Westmount, Canada

[21] Appl. No.: 768,730

[22] Filed: Dec. 18, 1996

Related U.S. Application Data

[63] Continuation-in-part of Ser. No. 570,919, Dec. 12, 1996, abandoned.
[51] Int. Cl.[6] .................................................. G01N 27/00
[52] U.S. Cl. .................. 324/71.4; 324/71.1; 324/717; 324/724; 164/4.1; 266/99
[58] Field of Search ........................... 324/71.1, 71.4; 266/16; 204/246

[56] References Cited

U.S. PATENT DOCUMENTS

| | | | |
|---|---|---|---|
| 3,755,126 | 8/1973 | Misener | 204/195 |
| 4,763,065 | 8/1988 | Hachey | 324/71.4 |
| 5,241,262 | 8/1993 | Guthrie | 324/71.1 |
| 5,567,286 | 10/1996 | Pal | 204/246 |

*Primary Examiner*—Ernest F. Karlsen
*Assistant Examiner*—Thomas Valone

[57] ABSTRACT

A molten metal inclusion sensor probe which is immersed in the molten metal and detects inclusions therein by the electric sensing zone method comprises inner and outer steel tubes disposed one within the other to form an annular gas containing space, the tubes being spaced apart from one another by electrically insulating spacing rings between the two tubes at or adjacent to the opposite ends thereof. The space is vented to the exterior of the outer tube, or in the case of a one-shot probe to the interior of the inner tube. A sensing zone member, which may also act to space the tube lower ends, is mounted by the tubes at their lower ends and provides the sensing zone orifice. In some embodiments the seals between the sensing zone member and the tube lower ends are maintained despite differences in expansion coefficients of the materials.

20 Claims, 5 Drawing Sheets

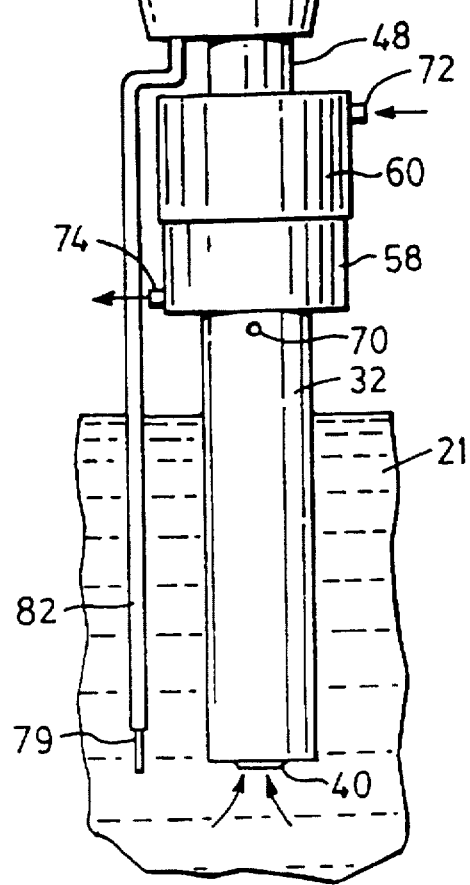
FIG. 1
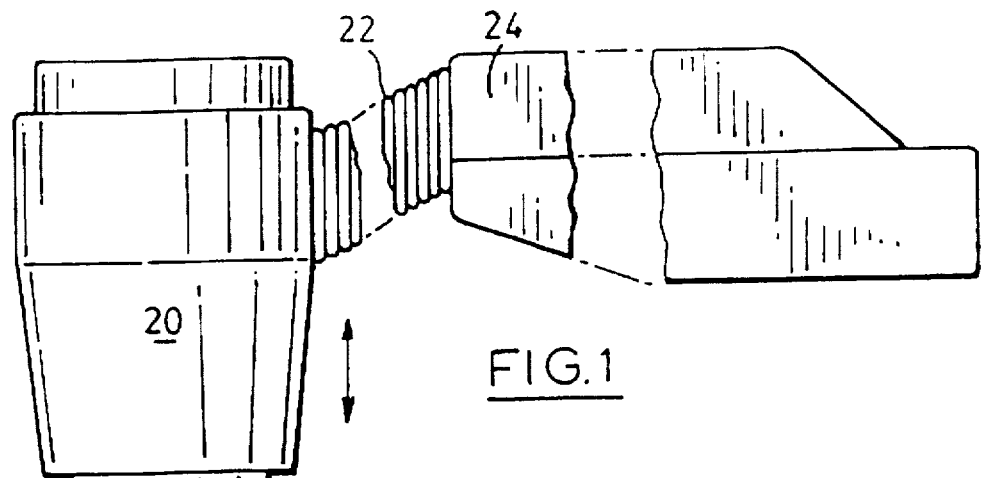
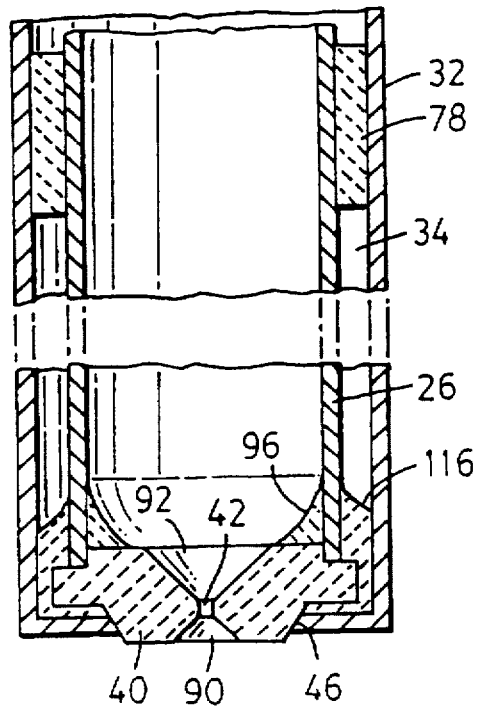
FIG. 8

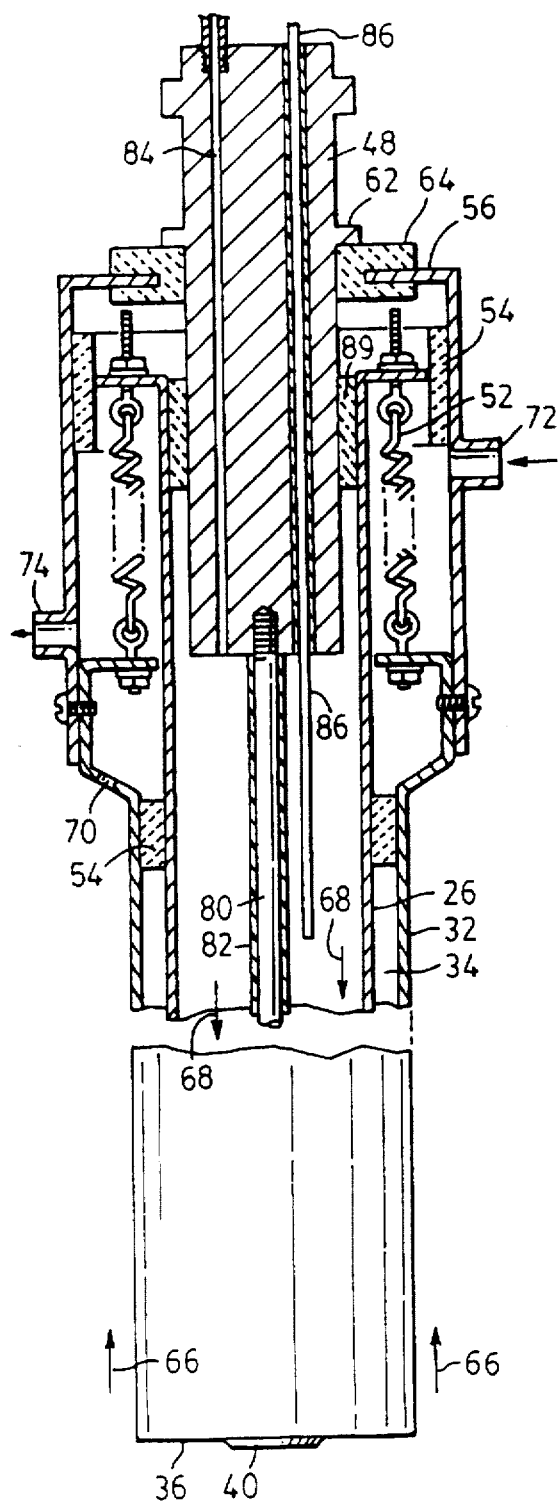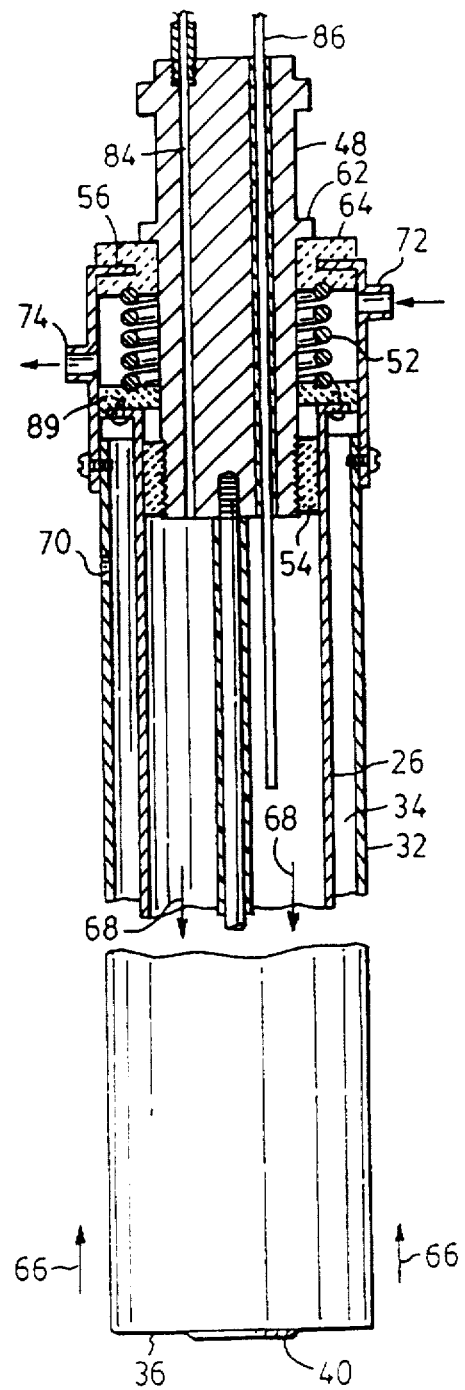

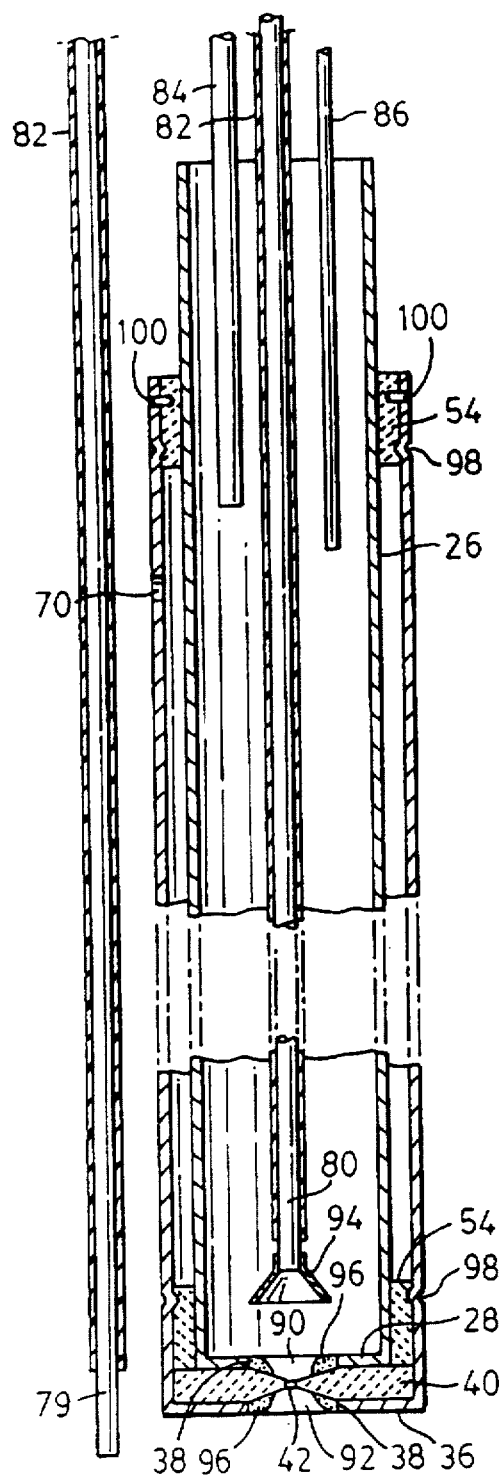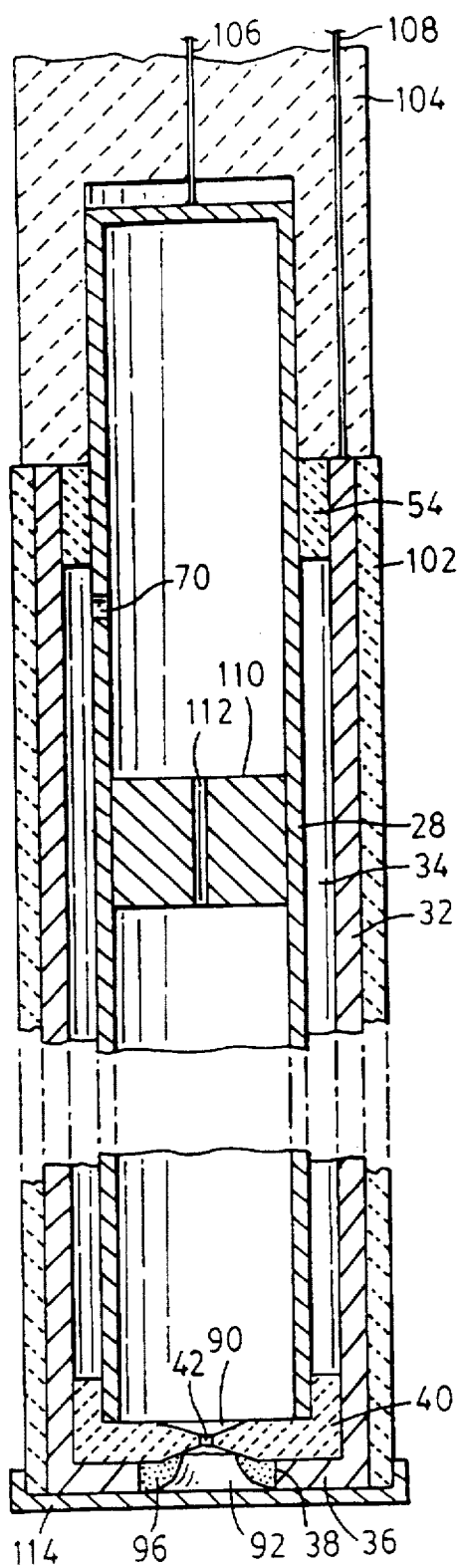

MOLTEN METAL INCLUSION SENSOR PROBES

CROSS REFERENCE TO RELATED APPLICATION

This application is a continuation-in-part of my prior application No. 08/570,919, filed Dec. 12, 1996, now abandoned.

FIELD OF THE INVENTION

This invention is concerned with improvements in or relating to molten metal inclusion sensor probes, namely sensor probes that are used in apparatus for detecting the number, size and size distribution of inclusions in molten metal, the apparatus employing what is now sometimes known as the ESZ (electric sensing zone) method.

Review of the Field

The production and refining of metals from their basic ores inevitably results in what, for convenience in nomenclature, are referred to as "inclusions", such as precipitated secondary phase particles, drops of slag and air bubbles, all of which have a more or less deleterious effect upon the technical properties of the metals. An even greater quantity and variety of inclusions may be found when scrap metal is being recycled and refined, either alone or as an addition to virgin metal, owing to the unavoidable presence of various products of oxidation and corrosion, dirt, oils, paint, etc. on the scrapped articles. The presence of such inclusions within the resultant rolled or cast products is generally undesirable from the point of view of properties such as fatigue life, toughness, corrosion, tearing, splitting, surface quality, pinholes, etc., particularly when larger inclusions (e.g., dimensions>20 microns) are present. It has therefore become more and more essential to know whether or not the metal is sufficiently "clean" for its intended purpose, and also to show whether or not the refining processes employed are producing sufficiently clean metal.

A quantitative measurement method and apparatus for such inclusions, particularly in molten aluminium, has now become well established in the aluminium industry, and is known as the LiMCA (Liquid Metal Cleanliness Analysis) system; these are described and claimed for example in U.S. Pat. Nos. 4,555,662, 4,600,880, and 4,763,065, the disclosures of which are incorporated herein by this reference. The application of the method and apparatus to the detection of inclusions during the refining and recycling of other metals is under investigation. The ESZ method was used prior to its application to molten metals to measure inclusions in aqueous solutions and relies upon the fact that any inclusion is usually of different conductivity (usually much lower) than the highly electrically conductive liquid metal in which it is entrained. A measured volume of the molten metal is passed through a sensing zone consisting of an orifice of specific size in an electrically insulating material; as an inclusion particle passes through the orifice the electrical resistance of the current path through the orifice changes in proportion to the volume of the inclusion, and this change is detected as an electrical potential pulse between two electrodes on opposite sides of the orifice. The amplitude of each pulse indicates the size of the respective inclusion, while the number of pulses indicates the number of inclusions in the sample volume.

Currently used sensing probes employ a sampling tube of electrically-insulating, heat-resistant material that is lowered into the metal, the tube forming a chamber into which the molten metal is sucked through a sensing zone orifice in or near to its lower end. The sensing electrodes may take the form of two rods disposed one inside and one outside the tube, or concentric tubes of a suitable conductive material applied to the inner and outer walls of the tube. In order for the ESZ method to operate successfully it is necessary that the electrical current path pass entirely through the electric sensing zone, and there should be no unwanted leakage between the liquid metal inside and outside the sampling tube. The materials used and proposed for the fabrication of the sensing probe tubes are all non-conducting and highly heat-resistant, such as borosilicate glass, alumino-silicate glass, fused silica, alumina, magnesia, mullite, boron nitride and other ceramic materials. Problems with these materials can be manifold, especially in view of the broad range of metals to which the system can be applied, including iron, steel, aluminium, copper, titanium, magnesium and alloys thereof. For example, chemical reaction often occurs between the metal and the material of the tube causing its rapid disintegration. As a specific example, a fused silica tube placed in molten magnesium will be attacked rapidly, since silica ($SiO_2$) is thermodynamically less stable than magnesia (MgO) and is therefore reduced by the magnesium, leading to relatively rapid disintegration of the tube, e.g. about two minutes for one of wall thickness of 1 mm. Molten copper containing dissolved oxygen causes similar problems, with the resulting copper oxide fluxing the silica (m.p. 1740° C.), and again causing rapid disintegration of the tube.

Other problems with refractory materials follow from the fact that many are brittle, making it difficult to produce robust, thin-walled tubes, and difficult to assemble, disassemble and maintain the equipment without high risk of damage and breakage. Further problems result from the thermal stresses that are generated in the tubes when they are immersed in the liquid metal; these stresses are particularly severe with liquid steel baths, typically operating at melt temperatures between 1500° C. and 1700° C., and it is not uncommon for the sample tubes to crack unless they are carefully preheated to a relatively high temperature. All of the refractory materials suitable for use as sample tubes are difficult to fabricate, so that the tubes made from them are correspondingly expensive, and the difficulty and expense increase disproportionately as the size of the sample tube is increased. Finally, all ceramic oxides tend to develop electrical conductivity at high temperatures that can become sufficiently high to compromise the electrical performance of the probe.

U.S. Pat. No. 4,763,065 referred to above discloses apparatus for the detection and measurement in a molten metal sample of suspended particulates, the apparatus comprising a container defined by a composite wall including electrically conducting inner and outer walls electrically insulated from one another and an electrically insulating barrier including a sensing zone passage. The electrically conducting walls comprise two concentric cylindrical metal tubes which also comprise the electrodes for the sensing zone. The upper ends of the tubes extend into a mounting block while the lower ends are provided with inwardly extending flanges between which the insulating barrier, which comprises a flat disc through which the sensing zone passage passes, is held by a pair of insulating discs. The specification states that the annular space between the tubes is filled with densely packed alumina, or with some other electrically insulating heat conducting material, or it could be left empty, or a heating element could be provided to ensure that the contents of the container remain molten.

3

Definition of the Invention

It is the principal object of the present invention to provide inclusion sensor probes for molten metals of new construction.

It is another principal object to provide such probes of inexpensive construction suitable for use for multi-shot measurements in the less severe environments of the lower melting point metals, and that can be sufficiently inexpensive that they are usable for one-shot measurement in higher melting point metals during which the probe is destroyed.

In accordance with the present invention there is provided a molten metal inclusion sensor probe of the type which is immersed in the molten metal and detects inclusions therein by the electric sensing zone method, the probe comprising:

an inner metal tube disposed within an outer metal tube, the tubes being electrically insulated from one another and forming an annular gas containing space between them;

a sensing zone member of electrically insulating heat resistant material mounted by the tubes and having therein an orifice comprising a sensing zone passage between the interior of the inner tube and the exterior of the outer tube;

spacing means of electrically insulating heat resistant material maintaining the tubes spaced from one another; and vent means venting the annular space through the wall of the outer tube to the exterior of the outer tube, or through the wall of the inner tube to the interior of the inner tube.

Such a sensor probe may comprise spring means operative between the inner and outer metal tubes and the sensing zone member to urge them for relative movement such as to maintain sealing contact of the metal tubes with the sensing zone member as the temperature of the sensor probe changes. Such spring means may comprise at least one tension spring connected between the metal tubes and urging them for longitudinal movement to maintain sealing contact of the metal tubes with the sensing zone member, or alternatively may comprise at least one compression spring interposed between the metal tubes and urging them for such longitudinal movement. The spring means may be disposed in the annular gas containing space between the inner and outer metal tubes.

The spacing between the two metal tubes may be in the range 2 mm–10 mm (0.08 in–0.40 in), preferably in the range 2 mm–5 mm (0.08 in–0.20 in).

The spacing means may comprise the sensing zone member at the ends of the metal tubes that are inserted into the molten metal and at least one ring-shaped spacer member at or adjacent to the other ends of the metal tubes; the sensing zone member may then have the form of a cup having the sensing zone orifice in the bottom wall thereof, the cup side wall constituting spacing means between the metal tubes. Alternatively the spacing means may comprise at least two ring-shaped spacer members at or adjacent to the opposite ends of the metal tubes, and preferably the total length of all of such spacing means is not more than 10% of the total length of the metal tubes.

Preferably the metal tubes are of low carbon steel and the wall thickness of the metal tubes is in the range 1 mm–2 mm (0.04 in–0.08 in). In a sensor probe intended for the measurement of inclusions in iron and steel the wall thickness of the outer metal tube may be in the range 4 mm–10 mm (0.16 in–0.40 in).

The inner surface of the outer metal tube and the outer surface of the inner metal tube facing one another across the gas containing space may be rough and/or provided with a black coating to increase the efficiency of heat transfer between them by radiation.

4

DESCRIPTION OF THE DRAWINGS

Molten metal inclusion sensor probes which are preferred embodiments of the invention will now be described, by way of example, with reference to the accompanying diagrammatic drawings, wherein:

FIG. 1 is a side elevation of electrical equipment as employed by a currently available LiMCA system for the measurement of inclusions in aluminium, and illustrating the use therewith of multi-shot sensor probes of the invention for the measurement of inclusions in lower melting point metals;

FIGS. 3–7 are cross-sections similar to FIG. 2 of sensor probes which are another and further embodiments of the invention, the lower portions of the sensor probes of FIGS. 3–5 being shown in side elevation; and FIG. 8 is a cross section of the lower end only of a sensor probe that is a still further embodiment of the invention to show a still further sensing zone member construction.

DESCRIPTION OF THE PREFERRED EMBODIMENTS

Figure 2:
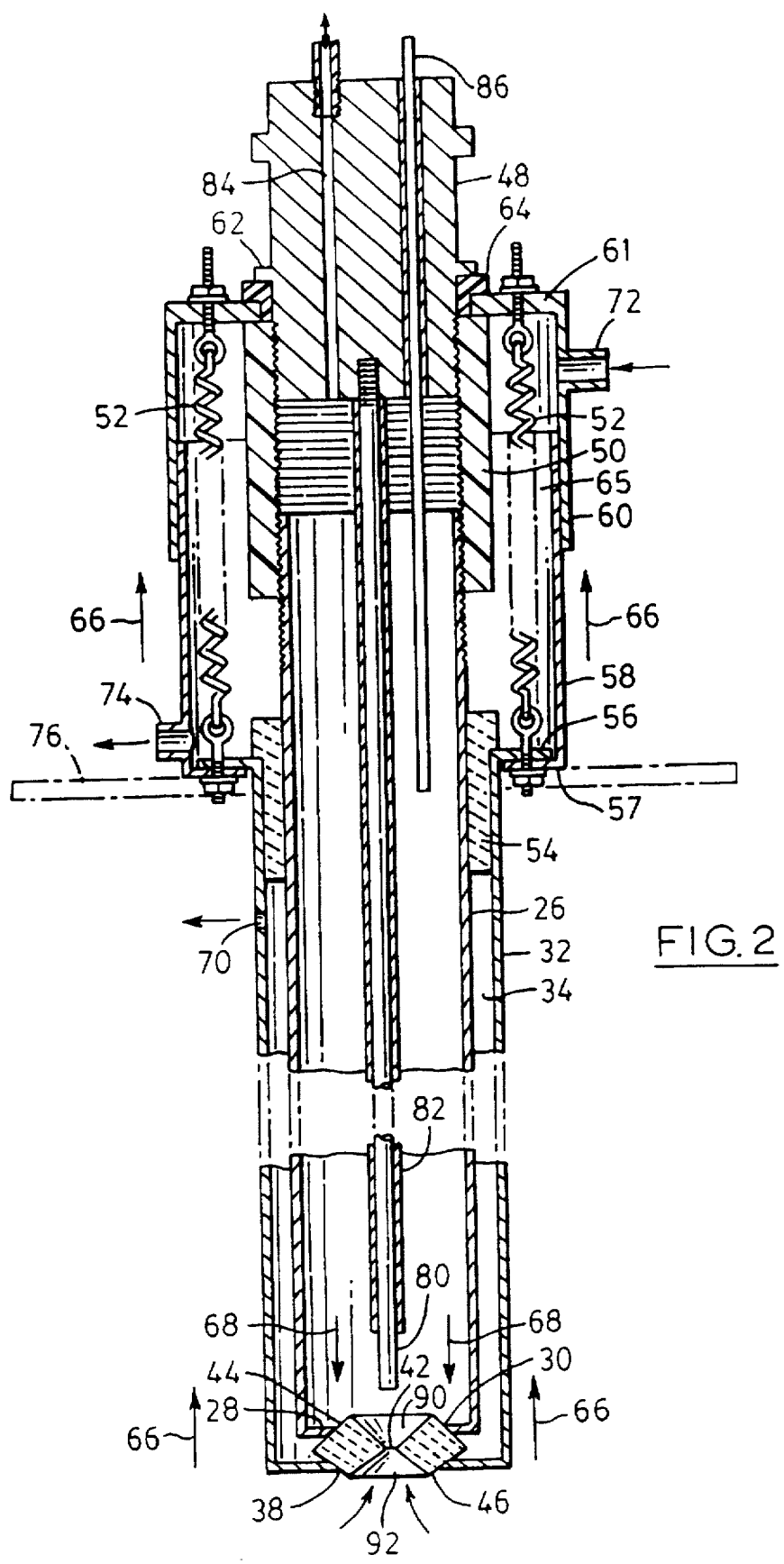
FIG. 2 is a longitudinal cross-section to a larger scale of the sensor probe only of FIG. 1.

The same reference number is used for similar parts of the different embodiments wherever that is possible.

The multi-shot sensor probe of FIG. 1 is intended for use in the measurement of inclusions in metals and alloys of lower melting points such as magnesium (650° C.–750° C.), aluminium (660° C.–750° C.), and copper (1083° C.–1300° C.). The sensor probe is mounted in a sensor head 20 so as to protrude vertically downward therefrom, the head enabling the probe to be lowered into and raised from a bath 21 of the molten metal. The head is connected for such movement by a linkage 22 to electrical apparatus 24 which receives electric signals from the sensor probe and uses them to determine whatever information is required as to the nature, size, size distribution and number of the inclusions detected by the sensor probe. The head and associated electrical apparatus can for example be the LiMCA II apparatus as sold by Bomem Inc. of Quebec City, Quebec, Canada, for inclusion detection in aluminium, such apparatus being shown and described in U.S. Pat. No. 5,130,639, issued 14 Jul., 1992 to Alcan International Limited, the disclosure of which is incorporated herein by this reference and to which further specific reference is made below.

The sensor probe comprises a cylindrical highly elongated first metal cup providing an inner cylindrical tube 26, the horizontal bottom 28 of the cup having an aperture 30 therein. A cylindrical highly elongated second metal cup of shorter length than the first cup surrounds the first cup and provides an outer cylindrical tube 32 that is coaxial with the inner tube, the two tubes together forming a vertically elongated annular hollow gas-containing space 34 between them. The horizontal bottom 36 of the second cup is parallel to that of the first cup and has an aperture 38 therein that registers with the aperture 30. A sensing zone containing disc 40 of a refractory material is sandwiched between the two cup bottoms and has therein an accurately formed orifice 42, very much smaller than the apertures 30 and 38, that constitutes the electric sensing zone passage through which the molten metal passes and in which the inclusions are detected. Besides providing this passage the disc 40 maintains the adjacent lower ends of the two tubes in their coaxial relationship, and to this end upper annular face 44 of the disc that is engaged by the circular edge of the aperture 30 is tapered upward to be of frusto-conical shape, while lower annular face 46 that is engaged by the circular edge of the aperture 38 is tapered downward to be also of frusto-conical shape and a mirror-image of the face 44. The edge of aperture 30 is spring pressed downward, by spring means which will be described below, into sliding butting contact with the downward sloping surface 38, and the edge of aperture 38 is spring pressed upward into sliding butting contact with the upward sloping surface 46, and the adjacent bottom ends of the two tubes 26 and 32 are thereby centred on the disc 40 so as to maintain the tubes coaxial with one another, despite changes in their dimensions with changes in their temperature and differential changes in their dimensions with differences in their temperatures. The inclined surfaces ensure that both longitudinal and radial changes in dimensions are accommodated.

This embodiment also relies solely upon the spring-urged contact between the circular aperture edges and the surfaces 44 and 46 that they butt against to seal the bottom end of the chamber 46 against entry of molten metal from the bath, especially when the sensor probe first enters the bath and there is maximum differential expansion between the relatively low expansion coefficient refractory material of the disc 40 and the relatively high expansion coefficient metal of the tubes. Maintenance of the seals in this manner is of particular importance in one-shot probes, where there is usually no opportunity to lower the probe slowly into the bath to try to minimize disruptive differential expansion forces affecting the seals. The edges of the apertures 30 and 38 are inclined so that they extend parallel to the respective disc surfaces 44 and 46 that they engage, so that the contact is surface to surface facilitating the sealing action between them.

The sensor probe is provided at its top end with a metal mounting member 48 of external diameter at its top end such that it fits within the mounting in the LiMCA II sensor head 20 for the ceramic tube based sensor probes currently used therewith. The bottom end of the mounting member is externally screw threaded and is screwed into the top end of an internally screw threaded cylindrical connector member 50 of electrically insulating material. The upper end of the inner metal tube 26 is externally screw threaded and is screwed into the bottom end of the connector member, so that this tube is rigidly connected to the mounting member 48 while electrically insulated therefrom. The outer metal tube 32 is mounted for longitudinal movement relative to the fixed inner tube, as will be described below, and so as to permit the application to the disc 40 of the centring and sealing spring force provided by four tension springs 52 (only two shown) spaced equidistantly circumferentially around the tubes 26 and 32. As few as two springs can be employed, although a minimum of three is preferred to ensure uniformity, and more than four can of course be used. An annular spacer ring 54 is a snug fit in the upper end of the outer tube 32 and is a close sliding fit on the immediately adjacent smooth cylindrical portion of the inner tube 26, this ring thus permitting the necessary relative longitudinal movements of the tubes while cooperating with the disc 40 in maintaining the tubes coaxial along their lengths. A flange 56 extends radially outwards from the top end of the outer tube 32 and is fastened to the annular bottom surface 57 of an upward opening cup-shaped member 58, the cylindrical body of which is a close sliding fit within the cylindrical body of a downward opening cup-shaped member 60. Annular bottom 61 of the member 60 extends radially outward from the mounting member 48 and is clamped between the connector member 50 and a radially outward extending locating flange 62, a washer 64 of electrically insulating material being interposed between the members 48 and 60 to maintain the two tubes electrically insulated from one another, so that the only electrical path between the metal in the bath and that inside the inner tube is through the sensing zone orifice 42.

The upper cup-shaped member 60 is therefore rigid with the mounting member 48 and the inner tube 26, while the lower cup-shaped member 58 is rigid with the outer tube 32 and the two cup-shaped members can move longitudinally relative to one another. The tension springs 52 are enclosed within an annular cross section chamber 65 formed between the cup-shaped members 58 and 60, and are connected at their ends between the bottoms of the members so as to urge the lower member 58 and the outer metal tube 32 to move upward in the direction of arrows 66, thereby producing a corresponding sealing force between the disc 40 and the butting circular edge of the outer tube 32, as indicated by the arrows 66. A corresponding reaction sealing force is produced between the disc 40 and the butting circular edge of the inner tube 26, as indicated by arrows 68. These seals are maintained by the springs despite the changes in temperature and dimensions of the different parts of the probe while it is suspended over the metal bath and as it is lowered into the bath, and despite the different rates of change for the parts of metal, as compared to those for the parts of refractory materials. Moreover, the seals are also maintained when, upon insertion of the sensor probe into the metal bath, the outer metal tube 32 is heated faster by its immediate full contact of its outer wall with the molten metal than is the inner metal tube 26, which is heated by radiation from the outer tube and by conduction from and direct contact with the molten metal as it slowly fills the tube interior through the very narrow sensing orifice.

A gas vent 70 connects the interior of the annular space 34 with the exterior of the outer metal tube 32, and is provided in the wall of the outer tube close to its top end and at a height sufficient to ensure that molten metal of the bath 21 cannot enter the annular space 34, the vent being essential to accommodate the relatively large expansion of gas that occurs within the space as it is heated. It is found with a probe sensor for use with these relatively low melting point metals that the connector member 50 and the spacer member 54 can be of relatively low melting point material, such as TEFLON (Trade Mark), although for extended life it may be preferred to make at least the spacer washer 54 of a ceramic or other refractory material. Screw threaded connectors connecting the ends of the springs 52 to the cup bottoms 57 and 61 permit adjustment of the tensions provided by the springs. The springs will weaken as they are heated and to maintain their strength at an adequate value without the need for initially greatly oversized springs cooling air may be provided which is pumped into the chamber 65 through an inlet 72, the heated air leaving the chamber through an outlet 74. In some embodiments it may be found to be sufficient to provide the sensor probe with a radially extending shield 76 (see FIG. 2) of a heat insulating and reflecting material positioned just below the lower cup-shaped member 58, the shield protecting the upper part of the probe from heat radiated from the bath 21, avoiding the need for an air pump and connecting tubing. In a sensor probe in which the metal tubes 26 and 32 are exceptionally long, so as to be able to reach more deeply into the bath, it may be found desirable to provide one or more short annular spacer rings, such as a centrally disposed ring 78 as shown in FIG. 8, between the spacer member 54 and the disc 40. Any such intermediate spacer rings must provide for free through passage of the gas present in the space 34.

Since the two metal tubes are electrically insulated from one another they could also constitute the sensing electrodes for the sensing system, in which case they would be electrically connected to suitable terminal assemblies within the head 20 by electric leads which are not shown. Even if the metal tubes are not used as electrodes they may still be electrically connected into the sensor head 20, for example in order to minimise background noise. In this embodiment it is preferred that the metal tube assembly only provide the container into which the molten metal is drawn through the sensing zone passage, and the required electrical measurements for the detection of inclusions are made between a pair of additional rod-shape electrodes 79 (FIG. 1) and 80. The electrode 79 is mounted directly in the sensor head 20 so as to extend parallel to the exterior of the outer tube 32, while the electrode 80 is mounted within the interior of the inner tube, coaxially therewith, and is screw threaded into the metal mounting member 48 by which it is electrically connected into the sensor head. Preferably these electrodes are coated with a thin life extending layer 82 of heat and electrically insulating material, such as boron nitride, except for small portions at their ends adjacent to the sensing zone passage 42. One of the difficulties encountered with ESZ apparatus is the extremely noisy electrical environments in which they must operate, and the low signal/noise ratios that are obtained, making accurate measurement of the pulses very difficult; it is also very desirable to be able to monitor continuously the size of the sensing zone aperture 42, since this is enlarged by the abrading action of the molten metal passing through it, and this also has a direct effect upon the sensitivity and accuracy of the measurement. Additional electrode configurations, employing up to five electrodes, that facilitate both of these measurements, and also the minimization of ground loop currents, is described in U.S. Pat. No. 5,130,639, referred to above.

In operation, initially the probe sensor is held above the bath for a period of at least a few minutes so as to be heated thereby, particularly the sensing zone member 40, so as to try to ensure that metal will not freeze in the aperture 42 as the probe is lowered into the bath. To the same end, as the sensor probe is lowered into the bath and for a period thereafter, an inert gas, such as argon, or an inert gas mixture, is supplied under pressure to the interior of the inner tube through an inlet/outlet tube 84 that extends through and is mounted by the mounting member 48. The gas bubbles out through the aperture 42 and maintains it and the tube interior free of metal until the sensing zone member and the probe interior are hot enough to ensure that the entering metal will not freeze. After a suitable period the supply of gas is stopped and instead a vacuum is drawn by a vacuum source (not shown) within the probe interior through the inlet/outlet tube 84, the vacuum sucking molten metal from the bath into the tube interior through the sensing zone passage 42 while the apparatus 24 records the number, size and size distribution of the particles detected. The drawing of the molten metal continues either for a predetermined period of time sufficient for the desired quantity of metal to be sampled, or until the molten metal contacts a level sensing electrode 86 within the probe, giving a signal to the apparatus that a sufficiently large sample has been tested. Since visual observation of the level within the sensor probe is not possible, in commercial equipment such a sensing means will usually be provided as a safety back-up system to the timing circuit to ensure that metal is not drawn into the sensing head.

Upon immersion of the probe the outer metal tube 32 will heat very rapidly to the melt temperature, while heat transfer by conduction, convection and particularly by radiation across the gas-filled chamber 34 must be sufficient to ensure that the inner tube will also heat up sufficiently rapidly for the entering metal to remain molten. This is important for efficient operation, since otherwise the sensor probe may need to be preheated for an undue length of time, or otherwise brought very close to its operating temperature before such immersion. If such blockage does occur it may be necessary to withdraw the probe from the bath in order to take the necessary corrective action. This is even more important when the sensor probe is intended for one-shot operation, a specific embodiment of which will be described below, since once freezing occurs there is usually no opportunity for correction before the probe is destroyed. The most efficient mode of heat transfer from the outer tube to the inner tube is by radiation across the gap between them, since this is operative along the whole length of the tubes, and particularly over the immersed portion of the outer tube. It is therefore important to ensure that the radiation view factor between the tubes is as close as possible to one (1), i.e. "black body" radiation levels are being obtained. To this end steps may be taken to make the facing outer surface of the inner tube and the inner surface of the outer tube as radiation efficient as possible, for example by roughening these surfaces if they are not sufficiently rough as received from the manufacturer, as for example by scoring, wire brushing, sand or shot blasting, and/or by coating them with a layer having a higher radiation coefficient than the metal, such as a layer of iron oxide, sulfide or carbide, or any other adherent refractory black coating.

Ensuring that the entering metal does not freeze is more difficult with ceramic tubes unless they are slowly and thoroughly preheated to a temperature close to the bath temperature, owing to the complete absence of the possibility of heat transfer by radiation, and to their very much lower heat conductivity inhibiting the passage of heat from the metal bath to the sample tube interior. In addition they are much more sensitive to breakage by thermal shock while being preheated and upon entering the bath. Owing to the negligible electrical conductivities at the operating temperatures of the gas in the chamber 34, especially as compared to some ceramics, correspondingly negligible amount of electrical current will pass between the concentric tubes through the chamber 34, and the current that does pass between them is correspondingly almost exclusively that passing between the electrodes 79 and 80 through the sensing zone aperture 42.

Since this embodiment is intended for multiple serial test operation, at the conclusion of each test the metal is driven from the probe interior while still molten by again injecting an inert gas, or inert gas mixture, under positive pressure through the inlet/outlet passage 84, when the test can be repeated.

Figure 3:
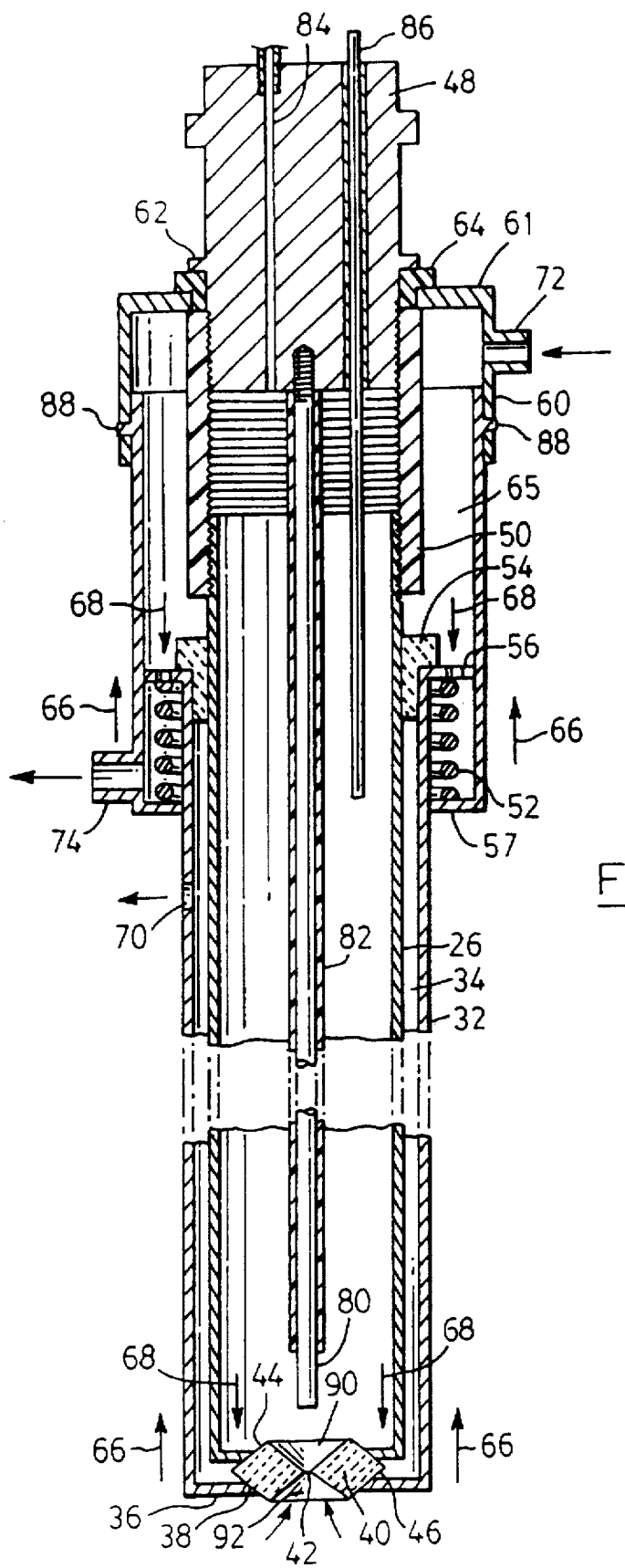

The second embodiment shown in FIG. 3 functionally is similar in operation to that shown in FIG. 2, the major difference being that the sealing butting contact of the metal tube edge surfaces against the disc faces 44 and 46 are produced by the action of a single compression spring 52 in place of the plurality of tension springs 52 of the first embodiment. The upward opening lower cup-shaped member 58 and the downward opening upper cup-shaped member 60 are connected together by a bayonet connection 88 that permits the probe to be disassembled when required but prevents any relative vertical movement between them. The compression spring is interposed between the annular radial flange 56 at the top end of the outer tube 32 and annular bottom surface 57 of the lower cup-shaped member 58, so that the relative vertical movement takes place between the outer tube and the lower cup-shaped member. Adjustment of the spring force can be accomplished by use of shim washers of different thicknesses that are interposed between the spring and the flange 56 and/or the flange 57. The single compression spring can be replaced by a plurality of smaller springs spaced circumferentially, and again a minimum of three is preferred.

It has been found that such cement-less pressure seals are extremely effective, to the extent that a prototype probe as illustrated by FIG. 2 performed flawlessly, permitting successive tests to be carried out successfully over a period of nearly two hours immersion in a magnesium melt. Moreover, when the tests were ended the tubes 26 and 32 and disc 40 were found to be intact and uncorroded. This may be contrasted with the experience with sample tubes of compacted silica which were used during initial experiments to test for inclusions in magnesium when they were found to be resistant to attack by liquid magnesium. It is believed that this resistance resulted from initial reaction of the surface with the melt to form a relatively impervious corrosion product layer. The sensing zone orifices were formed in inserts of boron nitride which were screw threaded into the tube walls. The tubes were found to be slightly porous and tended to crack easily due to thermal shock, the failure rate being from 10% to 50%, depending upon the porosity and grain size, so that finding the right batch of tubes to be used was somewhat a hit-or-miss problem and the tubes could not reliably be re-used.

FIGS. 4 and 5 show two further constructions for the upper portions of the sensor probes, that of FIG. 4 employing a plurality of springs, as with the embodiment of FIG. 2, while that of FIG. 5 employs a single spring, as with the embodiment of FIG. 3. These springs are accommodated in the upper part of the chamber 34 between the two tubes and the resulting probes are of smaller radial dimension. Such constructions are preferred for one-shot operation. In the embodiment of FIG. 4 the springs are connected between inward extending flange 56 corresponding to the outward extending flange 56 of the embodiment of FIG. 2, and outward extending flange 61 at the upper end of the inner tube 26, corresponding to the bottom 61 of the cup-shaped member 60 of the embodiment of FIG. 2. An additional annular spacer ring 54 is provided between the flange 61 and the inner wall of a cup-shaped extension of the outer tube 32, this extension taking the place of the cup-shaped member 60 of the embodiments of FIGS. 2 and 3. In the embodiment of FIG. 5 a single compression spring 52 is interposed between the annular washer 64 at the upper end of the outer tube and an annular washer 89 mounted on the flange 61 at the upper end of the inner tube 26. The different numbers of springs usable with the embodiments of FIGS. 2 and 3 are also usable with these embodiments.

A very satisfactory material for the tubes 26 and 32 is steel, preferably a low carbon mild steel (of the order of 0–1%, usually about 0.1% carbon), since the solubility of iron in molten magnesium or copper is minimal, and is still very low in molten aluminium. As described above, a rough unfinished surface is preferred to increase the radiation coefficient, whether or not a black highly radiative coating is also employed. It is also a suitable material for the electrodes 78 and 80 when magnesium is to be tested, since it is not attacked by magnesium. Other high melting point metals or alloys such as titanium, zirconium and INCONEL (Trade Mark) may also be employed, provided they are not unduly corroded by the molten metal, and provided that the available life justifies the higher cost. Steel is much cheaper than the equivalent quantity of a shaped refractory ceramic and the resultant sensor probes are more robust, resulting in a longer life during which they can be reused. The relatively simple disc 40 required for the sensing zone orifice 42, and the short, simple, robust spacer rings 54 and 78 require a minimum of material and are relatively inexpensive to manufacture, resulting in a sample tube that is stronger and more robust than an equivalent ceramic tube, and which is potentially much less expensive to manufacture, despite the need for the cup-shaped members 58 and 60 and the springs 52. A very suitable material for the disc 40 is boron nitride, which is not a particularly difficult material to work, the manufacturing operation required to produce the sensing zone orifice in a disc being much simpler than that required to form it in a long sample tube, while the scrap cost if the orifice is imperfect is correspondingly very much less.

Metals are inherently much less susceptible than ceramics to damage or destruction by thermal shock, even if some deformation results from the sudden heating. With the relatively high strength modulus of steel, even at the high temperatures of the molten metal, a minimum wall thickness for both tubes of about 1 mm (0.04 in) will be satisfactory. The radial dimension of the annular space 34 will be in the range 2 mm–10 mm (0.08 in–0.40 in), preferably 2 mm–5 mm (0.08 in–0.20 in), the dimension being as small as possible without the possibility of the tubes contacting one another, in the event of any shape distortion produced by the sudden elevation in their temperatures. A suitable outside diameter for the mounting member 48 so that it will fit in the apparatus head 20 is 2.5 cm (1 in). For measurements with magnesium an appropriate size for the molten metal samples is about 60 ml–100 ml, resulting in a column of metal within the inner tube interior of about 12.5–20 cm (5–8 ins) length, so that an appropriate minimum length of inner tube is about 25 cm (10 ins), resulting in a probe of about 45 cm (18 ins) overall length. If the metal to be sampled is iron or steel, as will be discussed below, the gas within the space 34 can be air. An atmosphere of argon or argon plus sulfur hexafluoride will be required for magnesium, while argon or nitrogen will be required for aluminium or copper.

Boron nitride has been used as the material for the sensing zone disc 40 but it can instead be any one of silicon nitride, aluminium nitride, magnesia or silica. The high-temperature electrically insulating materials used for the sensing disc 40 can also be used for the connector 50, the spacer ring 54, the washers 64 and 89, and any intermediate ring 78, in the event that it is not possible to use, or it is preferred not to use, a material such as TEFLON that is more sensitive to heat. The lower cost magnesia and silica are more appropriately used for elements that are not subjected to the wearing effect of the direct passage of the hot metal. In the embodiments to be described below the disc needs to be only a thickness of 1–5 mm (0.04–0.20 in), preferably 1–2 mm (0.04–0.08 in), but there is advantage in making it much thicker, e.g. in the range 1.5–2.5 cm (0.6–1.0 cm) so that, as shown in FIGS. 2 and 6, entrance 90 to the sensing zone passage, and also exit 92 therefrom, can be tapered towards the passage so as to ensure that the flow of metal through the passage is as streamlined as possible. Two values of included angle of 81° and 93° were tested without any noticeable difference in performance. The size of the sensing orifice 42 depends upon the metal under test, and the known nature of the inclusions to be detected, and is chosen to be reasonably larger (e.g. 2 times) than the largest inclusion particle expected to be encountered in the melt. The orifice will usually be of the order of about 300–350 microns for the lower melting point metals, and about 750 microns for iron and steel. It is found that a somewhat larger aperture is required for magnesium than for aluminium owing to the larger inclusions encountered and also the much greater number of inclusions found, believed to be due to the much higher oxidation potential of magnesium.

The embodiment of FIG. 6 is also one in which the metal tubes 26 and 32 are not used as the sensing electrodes, and instead they serve merely as a replacement for the ceramic sensing tube of the prior art apparatus, the sensing function being provided by a pair of electrodes 79 and 80. The inner electrode is provided with a splash guard 94 to divert the entering stream of molten metal. The sensing zone containing member comprises a thin flat disc 40 which is sandwiched between the horizontal bottoms 28 and 36 of the two tubes and extends the full width of the interior of the outer tube 32, the joints between the disc and the bottom surfaces being sealed with a suitable high temperature cement 96 (for example saureisen cement). The concentric spacing between the two tubes is maintained by an annular spacer ring 54 at the top end of the outer tube 32 and by a similar annular spacer ring 96 at the adjacent bottom ends of the two tubes and butting against the upper surface of the sensing zone disc 40. Owing to very different coefficients of thermal expansion of steel and most refractory materials suitable for use as the sensing zone disc difficulty may be experienced in maintaining the tightness of the cemented joints unless the probes are taken carefully through a heating protocol as described above to bring them as close as possible to their operating temperature while maintaining the integrity of the seals before immersing them in the molten metal bath. For example, the preferred material boron nitride has a coefficient of 0.87 µm/m/°C. perpendicular to the pressing direction and 2.95 µm/m/°C. parallel to the pressing direction, while steel has a coefficient of about 12 µm/m/°C. at 100° C. and about 15 µm/m/°C. at 700° C. The rings may be maintained mechanically in position along the tubes by crimping the tubes at various locations 98, as shown in the drawings, or by the use of radially extending fastening pins 100, or by any other suitable fastening means available for such high temperature apparatus. Typically the spacing rings will be of length in the range 1–2.5 cm (0.4–1.0 in), so that with two rings used with an inner tube of length proposed above the rings extend over a minimum of about 8% of the length of the tube, and a maximum of about 20%. If more than two rings are used then preferably their lengths are reduced so that together they do not occupy more than 25% of the length of the inner tube, and preferably they do not occupy more than 10% of the length.

FIG. 7 shows a sensor probe designed and intended for inclusion sampling in liquid iron and steel. Owing to the high melt temperatures involved (1500° C.–1700° C.), at high superheats (superheat=bath temperature minus freezing point or liquidus temperature) the outer tube 32 will quickly be severely eroded, and consequently such a probe must be considered to be a one-shot device, unless only used in steel melts at temperatures at which they are about to freeze. This is usually also the case with the known ceramic probes, and the potentially less expensive construction characteristic of the probes of the invention therefore makes them particularly suitable for such an application. The features of this embodiment that adapt it for single-use applications can be employed in the previously described multi-use embodiments when they are intended for single-use operation. In this embodiment the sensing zone member 40 has the form of a shallow ceramic cup or crucible the bottom of which contains the electric sensing zone orifice 42, and the side wall of which extends between the inner and outer steel tubes 26 and 32 to maintain them separated at their lower ends. The member therefore replaces the separate disc 40 and spacing ring 96 of the embodiment of FIG. 4. Such a shallow cup-shaped crucible is considerably more robust and is relatively inexpensive to make, so that the overall cost of the probe can be competitive with that of the highly elongated sample tubes required by the prior art probes. The inner metal tube is made somewhat thicker, of the order of 1.5 mm–2 mm (0.06 in–0.08 in) while the radial dimension of the annular space 34 remains about the same, and the thickness of the outer metal tube is greatly increased in proportion to the amount of superheat that is encountered, for example to at least 4 mm (0.16 in) for 50° C. superheat. This thickness should allow an immersion time of up to four minutes before the tubes melt sufficiently to fail and admit metal directly to the inner tube interior. By making the probe tubes of high quality, low carbon steel, contamination of the melt is not an issue, even though the probe is completely consumed. For a given superheat longer immersion times can be obtained by making the outer tube even thicker, but there is a practical limit to the potential increase beyond which the possibility of metal freezing in the aperture 42 and the lower part of the inner tube becomes too great, and the probe becomes too big and heavy. Another possibility is to add a cylinder 102 of thermal insulation over the outer tube 32 which will delay its destruction, but with added expense in manufacture, the possibility of adding undesired contaminants to the melt, and again increased possibility of freezing of the entering metal.

In this embodiment the two tubes 26 and 32 constitute the sensing electrodes while the probe is detachably connected to the lower end of an elongated support member 104, such as a lance, which enables the probe to be thrust safely manually by an operator into the furnace. The inner and outer tubes are therefore connected to respective electric leads 106 and 108 which pass upward through the lance to the measuring apparatus. Since the annular space 34 cannot in such an embodiment be vented to the ambient atmosphere it is instead vented by the bore 70 to the interior of the inner tube 26. The inner tube is closed at the top end and the sensor is assembled with sufficient vacuum within its interior to eliminate the need for an external vacuum source that would otherwise require a tube to extend through the lance. In other embodiments which are not specifically illustrated such a single-use disposable sensor probe is designed as a "bomb" which is connected to the electrical apparatus by a flexible cable, and which is thrown into the furnace containing the melt. Design requirements for such probes, are described, for example, in PCT application No. PCT/CA90/00140, International Publication No. WO90/13014, the disclosure of which is incorporated herein by this reference.

As with the other embodiments described above the probe will usually be preheated before it is immersed to ensure that the entering metal does not freeze. In addition the aperture 42 may be closed by a thin cap 114 of a material that melts much faster than those of the outer tube 32 and the cylinder 102, such as high carbon iron or aluminium. The cap closes the aperture until it melts after a period determined by its thickness, giving an opportunity for the sensing zone member 40 and the inner tube to heat to a suitable operating temperature before the metal enters the probe interior under the urge of the internal vacuum.

Provision may be made in such sensor probes for a fixed sample of the molten metal to be drawn into the probe body by placing a chill block 110 at the desired level within the inner steel tube 26, the block dividing the tube interior into upper and lower compartments which are connected by a narrow bore 112 of about 1 mm (0.04 in) diameter. The bore allows the vacuum in the upper compartment to be effective in drawing metal into the lower compartment, but the block is sufficiently large, and the bore is sufficiently small that the molten metal will freeze in it and prevent further metal being drawn into the probe when a sample of the volume of the lower compartment has entered the probe interior.

FIG. 8 shows another construction for the lower end of the probe, in which the horizontal bottom 28 of the inner metal tube has been eliminated and the tube end is closed by the sensing zone disc 40. The disc is provided with a downward tapered surface 46 which centres the disc in the outer metal tube aperture 38 and it is cemented to the bottom end of the tube by a fillet of a refractory cement 96. The spacing means at this end is completed by a ring 116 of a castable refractory cement, the material also entering any space that exists between the disc 40 and the tube bottom 36 to seal against entry of liquid metal from the bath other than through the sensing zone orifice 42.

I claim:

1. A molten metal inclusion sensor probe of the type which is immersed in the molten metal and detects inclusions therein by the electric sensing zone method, the probe comprising:
    an inner metal tube disposed within an outer metal tube, the tubes being electrically insulated from one another and forming an annular gas containing space between them;
    a sensing zone member of electrically insulating heat resistant material mounted by the tubes and having therein an orifice comprising a sensing zone passage between the interior of the inner tube with the exterior of the outer tube;
    spacing means of electrically insulating heat resistant material between the tubes and maintaining them spaced from one another;
    vent means venting the annular space through the wall of the outer tube to the exterior of the outer tube, or through the wall of the inner tube to the interior of the inner tube; and
    spring means operative between the inner and outer metal tubes and the sensing zone member to urge them for relative movement such as to maintain sealing contact of the metal tubes with the sensing zone member as the temperature of the sensor probe changes.

2. A sensor probe as claimed in claim 1, wherein the spring means are disposed in the annular gas containing space between the inner and outer metal tubes.

3. A sensor probe as claimed in claim 1, wherein spacing means between the inner and outer metal tubes also mounts them for longitudinal movement relative to one another;
    wherein each metal tube has a spring engaging member extending radially outward therefrom; and
    wherein the spring means comprises at least one tension spring connected between the radially extending spring engaging members and urging the metal tubes for such longitudinal movement to maintain the sealing contact of the metal tubes with the sensing zone member as the temperature of the sensing zone member changes.

4. A sensor probe as claimed in claim 1, wherein spacing means between the inner and outer metal tubes also mounts them for longitudinal movement relative to one another;
    wherein each metal tube has a spring engaging member extending radially outward therefrom; and
    wherein the spring means comprises at least one compression spring interposed between the radially extending spring engaging members and urging the metal tubes for such longitudinal movement to maintain the sealing contact of the metal tubes with the sensing zone member as the temperature of the sensing zone member changes.

5. A sensor probe as claimed in claim 1, wherein the sensing zone member has a first surface of frusto-conical shape that is butted by a circular end edge of the inner metal tube and a second surface of frusto-conical shape that is butted by a circular end edge of the outer metal tube, the two frusto-conical surfaces tapering inward away from one another, the spring means maintaining sealing engagement between the frusto-conical surfaces and the butting circular end edges of the metal tubes.

6. A sensor probe as claimed in claim 1, and comprising a first downward opening cup-shaped member operative with the inner metal tube and a second upward opening cup-shaped member operative with the outer metal tube, the cup-shaped members fitting one within the other to constitute a chamber enclosing the spring means.

7. A sensor probe as claimed in claim 6, and comprising means for feeding cooling air into the chamber enclosing the spring means.

8. A sensor probe as claimed in claim 1, wherein the spacing between the two metal tubes is in the range 2 mm–10 mm (0.08 in–0.40 in).

9. A sensor probe as claimed in claim 8, wherein the spacing between the two metal tubes is in the range 2 mm–5 mm (0.08 in–0.20 in).

10. A sensor probe as claimed in claim 1, wherein the spacing means comprise the sensing zone member at the ends of the metal tubes that are inserted into the molten metal and at least one ring-shaped spacer member at or adjacent to the other ends of the metal tubes.

11. A sensor probe as claimed in claim 10, wherein the sensing zone member has the form of a cup having the sensing zone orifice in the bottom wall thereof, the cup having a side wall that constitutes the spacing means between the metal tubes.

12. A sensor probe as claimed in claim 1, wherein the spacing means comprise at least two ring-shaped spacer members at or adjacent to the opposite ends of the metal tubes.

13. A sensor probe as claimed in claim 1, wherein the total length of all of the spacing means is not more than 10% of the total length of the metal tubes.

14. A sensor probe as claimed in claim 1, wherein the metal tubes are of low carbon steel.

15. A sensor probe as claimed in claim 1, wherein the wall thickness of the metal tubes is in the range 1 mm–2 mm (0.04 in–0.08 in).

16. A sensor probe as claimed in claim 1, and intended for the measurement of inclusions in iron and steel, wherein the wall thickness of the outer metal tube is in the range 4 mm–10 mm (0.16 in–0.40 in).

17. A sensor probe as claimed in claim 1, wherein the sensing zone member is a thin flat disc of thickness in the range 1 mm–5 mm (0.04 in–0.20 in).

18. A sensor probe as claimed in claim 1, wherein the sensing zone member is a disc of thickness in the range 1.5–2.5 cm (0.6–1.0 cm), the entrance to the sensing zone passage and the exit therefrom being tapered towards the passage for the flow of molten metal through the passage to be as streamlined as possible.

19. A sensor probe as claimed in claim 1, wherein the inner surface of the outer metal tube and the outer surface of the inner metal tube facing one another across the gas containing space are rough to increase the efficiency of heat transfer between them by radiation.

20. A sensor probe as claimed in claim 1, wherein the inner surface of the outer metal tube and the outer surface of the inner metal tube facing one another across the gas containing space are provided with a black coating to increase the efficiency of heat transfer between them by radiation.

* * * * *